(12) United States Patent
Hirschl et al.

(10) Patent No.: US 10,213,231 B2
(45) Date of Patent: Feb. 26, 2019

(54) SYSTEM AND METHOD FOR REDUCING AND STABILIZING A BONE FRACTURE

(71) Applicant: Life Spine, Inc., Huntley, IL (US)

(72) Inventors: Robert A. Hirschl, Clive, IA (US); Adam N. Goon, Eden Prairie, MN (US)

(73) Assignee: Life Spine, Inc., Huntley, IL (US)

( * ) Notice: Subject to any disclaimer, the term of this patent is extended or adjusted under 35 U.S.C. 154(b) by 112 days.

(21) Appl. No.: 14/606,549

(22) Filed: Jan. 27, 2015

(65) Prior Publication Data
US 2015/0209082 A1 Jul. 30, 2015

Related U.S. Application Data

(60) Provisional application No. 61/932,616, filed on Jan. 28, 2014.

(51) Int. Cl.
| | | |
|---|---|---|
| *A61B 17/68* | (2006.01) | |
| *A61B 17/70* | (2006.01) | |
| *A61B 17/86* | (2006.01) | |

(52) U.S. Cl.
CPC .......... *A61B 17/683* (2013.01); *A61B 17/70* (2013.01); *A61B 17/863* (2013.01); *A61B 17/8665* (2013.01); *A61B 2017/681* (2013.01); *A61B 2017/867* (2013.01)

(58) Field of Classification Search
CPC . A61B 17/683; A61B 17/863; A61B 17/8665; A61B 17/7216; A61B 17/7225; A61F 2002/0829; F16B 37/0807; F16B 37/0842; F16B 37/085
See application file for complete search history.

(56) References Cited

U.S. PATENT DOCUMENTS

| | | | | |
|---|---|---|---|---|
| 1,069,451 | A * | 8/1913 | Marston | .................. F16B 37/02 411/434 |
| 4,728,236 | A * | 3/1988 | Kraus | ................. F16B 37/0842 24/662 |
| 4,796,612 | A * | 1/1989 | Reese | .................. A61B 17/683 606/324 |
| 5,226,767 | A | 7/1993 | Foerster, Jr. | |
| 5,302,070 | A * | 4/1994 | Kameyama | ......... F16B 37/0842 411/437 |
| 5,390,683 | A | 2/1995 | Pisharodi | |
| (Continued) | | | | |

FOREIGN PATENT DOCUMENTS

WO    WO-2006/105437 A2    10/2006

OTHER PUBLICATIONS

Written Opinion of the International Searching Authority for Application No. PCT/US10/44223, dated Sep. 17, 2010, 5 pages.

*Primary Examiner* — Jacqueline T Johanas
(74) *Attorney, Agent, or Firm* — Foley & Lardner LLP

(57) ABSTRACT

A spinal implant system includes an elongated implant defining a distal portion interconnected to a proximal portion. The distal portion includes a set of threads for joining the distal portion with a distal part of the bone fracture. The system also includes a compression device coupled to the proximal portion of the elongated implant. The compression device is movable from an end of the proximal portion towards the distal portion of the elongated implant, wherein the compression device is structured to apply a compression force to a proximal part of the bone fracture.

20 Claims, 9 Drawing Sheets

(56) References Cited

U.S. PATENT DOCUMENTS

| | | | |
|---|---|---|---|
| 5,658,335 A | 8/1997 | Allen | |
| 5,658,337 A | 8/1997 | Kohrs et al. | |
| 5,906,464 A * | 5/1999 | Wedenig | F16B 37/0842 411/433 |
| 5,989,255 A * | 11/1999 | Pepper | A61B 17/8685 606/306 |
| 5,997,538 A * | 12/1999 | Asnis | A61B 17/8625 606/301 |
| 5,997,541 A * | 12/1999 | Schenk | A61B 17/68 606/104 |
| 6,126,689 A | 10/2000 | Brett | |
| 6,176,882 B1 | 1/2001 | Biedermann et al. | |
| 6,338,732 B1 * | 1/2002 | Yang | A61B 17/7291 606/311 |
| 6,375,682 B1 | 4/2002 | Fleischmann et al. | |
| 6,409,766 B1 | 6/2002 | Brett | |
| 6,491,724 B1 | 12/2002 | Ferree | |
| 6,494,883 B1 | 12/2002 | Ferree | |
| 6,537,320 B1 | 3/2003 | Michelson | |
| 6,558,389 B2 * | 5/2003 | Clark | A61F 2/0805 606/232 |
| 6,648,917 B2 | 11/2003 | Gerbec et al. | |
| 6,773,460 B2 | 8/2004 | Jackson | |
| 6,951,561 B2 * | 10/2005 | Warren | A61B 17/68 606/328 |
| 7,044,953 B2 * | 5/2006 | Capanni | A61B 17/8685 606/309 |
| 7,059,022 B2 * | 6/2006 | Yuta | B60R 13/011 24/297 |
| 7,087,055 B2 | 8/2006 | Lim et al. | |
| 7,344,564 B2 | 3/2008 | Sweeney | |
| 7,731,751 B2 | 6/2010 | Butler et al. | |
| 7,811,331 B2 | 10/2010 | Johnson et al. | |
| 7,998,176 B2 * | 8/2011 | Culbert | A61B 17/1671 606/247 |
| 8,439,620 B2 * | 5/2013 | Mellyn | F16B 37/0807 411/188 |
| 8,920,095 B2 * | 12/2014 | Baugh, Sr. | F16B 19/00 411/512 |
| 8,998,954 B2 | 4/2015 | Hartsell et al. | |
| 9,190,821 B2 * | 11/2015 | Kwasiborski | H02G 3/32 |
| 9,243,657 B2 * | 1/2016 | McCorkell | B60J 5/0468 |
| 2004/0106925 A1 * | 6/2004 | Culbert | A61B 17/0401 606/312 |
| 2004/0153156 A1 | 8/2004 | Cohen et al. | |
| 2004/0158244 A1 * | 8/2004 | Clark | A61F 2/0805 606/60 |
| 2004/0167625 A1 | 8/2004 | Beyar et al. | |
| 2005/0033437 A1 | 2/2005 | Bao et al. | |
| 2005/0131536 A1 | 6/2005 | Eisermann et al. | |
| 2005/0143827 A1 | 6/2005 | Globerman et al. | |
| 2005/0228391 A1 | 10/2005 | Levy et al. | |
| 2006/0084988 A1 | 4/2006 | Kim | |
| 2006/0085070 A1 | 4/2006 | Kim | |
| 2006/0095136 A1 | 5/2006 | McLuen | |
| 2006/0189999 A1 | 8/2006 | Zwirkoski | |
| 2006/0224241 A1 | 10/2006 | Butler et al. | |
| 2007/0179505 A1 * | 8/2007 | Culbert | A61B 17/0401 606/326 |
| 2009/0112318 A1 | 4/2009 | Butler et al. | |
| 2009/0198337 A1 | 8/2009 | Phan | |
| 2009/0240335 A1 | 9/2009 | Arcenio et al. | |
| 2009/0306715 A1 | 12/2009 | Jackson et al. | |
| 2010/0104394 A1 * | 4/2010 | Kwasiborski | F16B 37/0842 411/247 |
| 2010/0174373 A1 | 7/2010 | Galley et al. | |
| 2010/0204700 A1 * | 8/2010 | Falahee | A61B 17/1671 606/80 |
| 2010/0222816 A1 | 9/2010 | Gabelberger et al. | |
| 2010/0305705 A1 | 12/2010 | Butler et al. | |
| 2011/0035011 A1 | 2/2011 | Cain | |
| 2011/0213422 A1 * | 9/2011 | Gannoe | A61B 17/683 606/300 |
| 2012/0226322 A1 * | 9/2012 | Gonzalez-Hernandez | A61B 17/683 606/286 |
| 2014/0072386 A1 * | 3/2014 | Baugh, Sr. | F16B 19/00 411/337 |
| 2014/0121714 A1 * | 5/2014 | Hernandez | A61F 2/4081 606/319 |
| 2014/0328644 A1 * | 11/2014 | McCorkell | B60J 5/0468 411/107 |
| 2015/0209082 A1 * | 7/2015 | Hirschl | A61B 17/683 606/279 |
| 2015/0377276 A1 * | 12/2015 | Porter | F16B 41/002 411/366.1 |
| 2017/0045073 A1 * | 2/2017 | Liu | F16B 21/073 |
| 2017/0128109 A1 * | 5/2017 | Blain | A61B 17/7064 |

\* cited by examiner

SYSTEM AND METHOD FOR REDUCING AND STABILIZING A BONE FRACTURE

CROSS-REFERENCE TO RELATED APPLICATIONS

This application claims the benefit of priority to U.S. Provisional Patent Application No. 61/932,616 entitled "DEVICE FOR REDUCING AND STABILIZING A BONE FRACTURE, MORE PARTICULARLY, FOR IMMOBILIZING AND REDUCING FRACTURES OF THE C2 VERTEBRAE," filed Jan. 28, 2014, which is incorporated herein by reference in its entirety.

FIELD

The present disclosure relates to systems and devices for stabilizing and reducing a bone fracture. More particularly, the present disclosure relates to systems and devices for immobilizing and/or reducing fractures of the C2 vertebrae.

BACKGROUND

This section is intended to provide a background or context to the disclosure recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Spinal implants are typically used to treat spinal injuries. Because of various circumstances such as injury, trauma, or the like, it becomes necessary to immobilize and/or reduce a fractured bone. One specific fracture is of the second bone in the cervical spine, which is referred to as a type II odontoid fracture. Various devices have been devised in order to accomplish treat the type II odontoid fracture, most notably an odontoid screw.

While the conventional odontoid screw systems are beneficial, there are several undesirable features of the currently available odontoid screw that is used for surgical stabilization of a type II odontoid fracture. First, the conventional odontoid screw relies solely on the power of the lag screw to reduce the fracture. Often, the lag screw itself lacks the ability to reduce such a fracture. Second, predicting the correct length of lag screw is extremely important, but also extremely difficult. If the odontoid screw is too short, the screw will not get bicortical purchase. Screws that do not have bicortical purchase have a much higher failure rate. If the screw is too long, the screw could injure the brainstem, or important vascular structures. This can have unwanted and undesirable consequences. With the current odontoid screw technology, it is very difficult to select the correct screw length prior to insertion as the current odontoid screws come in pre-cut sizes (e.g., 2 millimeter increments). Other forms of surgical stabilization for a type II odontoid fracture is to fixate and fuse C1 to C2, or occipital cervical fusion. Both of these options significantly reduce and restrict the patient's ability to move their head and neck.

Accordingly, in view of the above, it can be appreciated that it would be desirable to have a better device, method and manner of immobilizing and reducing a type II odontoid fracture

SUMMARY

One embodiment relates to a spinal implant system for a type II odontoid bone fracture. The system includes an elongated implant defining a distal portion interconnected to a proximal portion, the distal portion including a set of threads for joining the distal portion with a distal part of the bone fracture. The system also includes a compression device coupled to the proximal portion of the elongated implant. The compression device is movable from an end of the proximal portion towards the distal portion of the elongated implant, wherein the compression device is structured to apply a compression force against a proximal part of the bone fracture. Thus, the spinal implant system is structured to provide at least two types of compression forces to the bone fracture: a first force provided by the threads of the distal portion and a second force provided by the compression device. This dual force characteristic allows the spinal implant system to provide a relatively greater compression force than threads on the distal portion alone.

Another embodiment relates to a spinal implant system for reducing or immobilizing bone fractures. The system includes an elongated implant defining a distal portion interconnected to a proximal portion, the distal portion including a set of threads for joining the distal portion with a distal part of the bone fracture and the proximal portion including a plurality of ribs. The spinal implant system also includes a compression device coupled to the proximal portion of the elongated implant. The compression device is movable from an end of the proximal portion towards the distal portion of the elongated implant, wherein the compression device is structured to apply a compression force against a proximal part of the bone fracture.

Still another embodiment relates to a method of reducing or immobilizing bone fractures. The method includes providing a spinal implant, the spinal implant having an elongated body with a distal portion and a proximal portion; inserting the distal portion of the elongated body into a distal part of a bone fracture; moving a compression device along the proximal portion of the elongated body toward the distal portion to make contact with a proximal part of the bone fracture; and adjusting a position of the compression device to control a compression force provided by the compression device on the proximal portion of the bone fracture.

DETAILED DESCRIPTION

Figure 1:
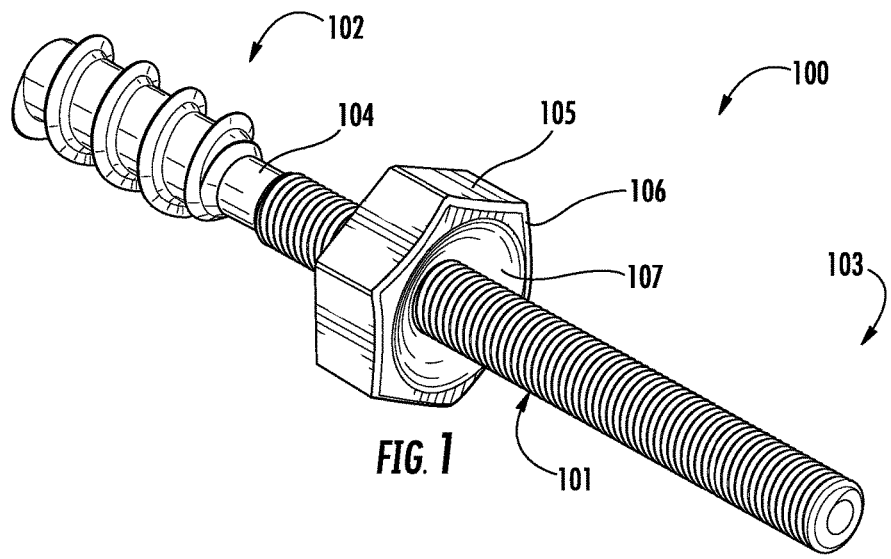
FIG. 1 is a perspective view of a spinal implant system, according to an exemplary embodiment.

Referring to Figures generally, a spinal implant system is shown according to various embodiments herein. The spinal implant system includes an implant that includes a distal portion, a proximal portion, and a compression device coupled to the implant. In one embodiment, the distal portion includes a threaded portion that joins with a distal portion of a bone fracture. The proximal portion may also include threads that permit engagement with threads of the compression device. Accordingly, the compression device is structured to rotatably translate on the proximal portion via the engagement of the threads. In operation, the distal portion is at least partly received in a distal bone fragment and the proximal portion is at least partly received in a proximal bone fragment. After insertion, the compression device is moved from an end of the proximal portion towards the distal portion of the body. In doing so, the compression device applies a compression force to the proximal bone fragment which acts to compress the proximal bone fragment towards the distal bone fragment (e.g., minimizes the bone fracture gap). After the compression device is in a position that applies the desired amount of compression force, a cutting device removes the excess length of the proximal portion of the shaft.

Advantageously, by utilizing a compression device, the spinal implant of the present disclosure is able to provide a relatively greater amount of compression force to a bone fracture, particularly a type II odontoid fracture, than conventional devices. This is due to the compression force not being a product of an odontoid screw alone. Rather, the compression force generated from the spinal implant system of the present disclosure is a product of both the spinal implant and the compression device. Furthermore, because the compression device is translatable on the proximal portion, a user may selectively control the amount of compression force provided. This may be beneficial if the implant is intended to provide a certain compression force for a certain amount of time and then a different amount of compression force for another amount of time. Further, this characteristic may eliminate the need for multiple implants being utilized for a bone fracture, where each implant corresponds with a different applied force. For example, after a bone fracture, the compression device may apply a force to hold the distal and proximate portions at a gap that is intended to not further the injury. Over a few weeks, the distal and proximal portions may acclimate/recover to that position, such that more compression is needed in order to fully treat the fracture. The compression device may then be adjusted for this purpose.

By utilizing a cutting device, the need to correctly predict and select an odontoid screw length is alleviated. Once the implant is placed to the desired length, it is severed, broken-off, disconnected, and/or cut in vivo at that position. Accordingly, the spinal implant of the present disclosure provides modularity to bone fractures and, more particularly, to type II odontoid fractures. The desirable effect is that a surgeon or technician may advantageously be primarily only concerned with the insertion process of the implant and not whether the selected implant is correct for this particular fracture. These and other features and advantages of the spinal implant system of the present disclosure are described herein below.

Figure 2:
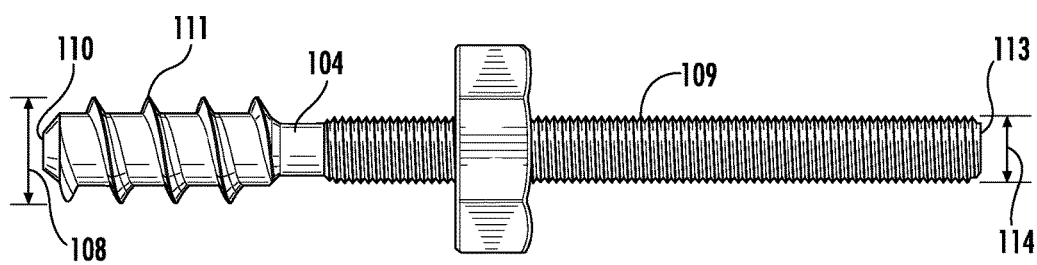
FIG. 2 is a side view of the spinal implant system of FIG. 1.
Figure 3:
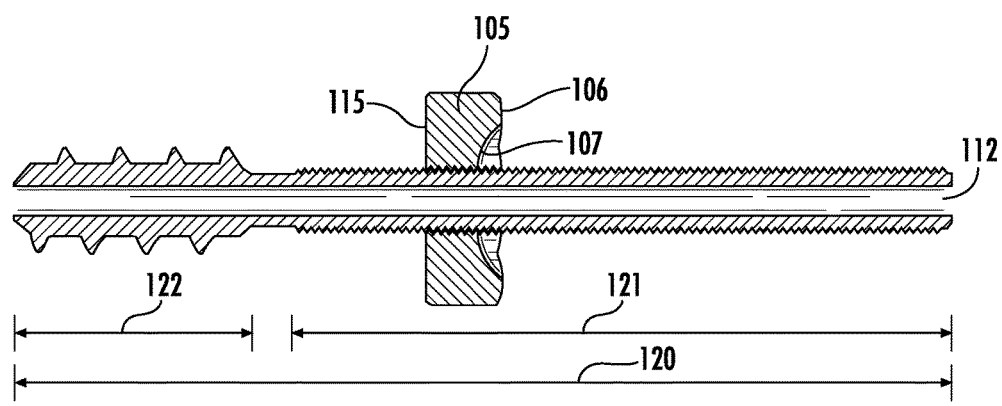
FIG. 3 is a side cross-sectional view of the spinal implant system of FIG. 1.

Referring now collectively to FIGS. 1-3, a spinal implant system 100 is shown according to one embodiment. As described herein, in one embodiment, the spinal implant system 100 is structured to reduce and/or immobilize a fracture. For example, the spinal implant system 100 would be used with a patient having a type II odontoid fracture with a gap separating the vertebral body of C2 and the distal portion of the tip of the odontoid fracture. The spinal implant system 100 may be constructed from any biocompatible material including, but not limited to, titanium, PEEK (polyetheretherketone), stainless steel, and the like.

As shown, the spinal implant system 100 includes an implant, shown as an elongated body 101. The elongated body 101 has a distal portion 102 and a proximal portion 103 interconnected by a transition portion 104. While shown as cylindrical (e.g., a tube, a cylinder, a rod, a shaft, a pipe, etc.), the elongated body 101 may be any shape (e.g., a rectangular prism) that is capable of connecting a distal portion of a bone fracture to a proximal portion of the bone fracture. As shown, the elongated body 101 defines a passage 112 (e.g., hole, channel, conduit, etc.) that is coaxial within the body 101. The passage 112 extends from a distal end 110 of the distal portion 102 to a proximal end 113 of the proximal portion 103. Accordingly, the passage 112 extends the full longitudinal length 120 of the body 101 (shown in FIGS. 2-3). The passage 112 is structured to receive a guide wire (e.g., a kirschner wire or pin) to insert the implant 101 on a desired trajectory to reduce or immobilize the bone fracture.

The distal portion 102 includes threads 111 and the distal end 110. The distal end 110 is located furthest from the transition portion 104 and corresponds with one end of the body 101. As shown, the distal end 110 is a relatively flat or blunt surface. After insertion in the bone fracture, the blunt distal end 110 is relatively less likely to adversely interact with the distal bone fracture to cause bone chips and the like. In this configuration, the threads 111 may be structured as lag-type threads (e.g., relative larger and coarser threads compared to conventional screw threads). Accordingly, a pilot hole may be drilled in the distal and proximal bone fractures prior to inserting the distal portion 102. However, in other embodiments, the threads 111 may be structured as any thread type capable of joining or engaging with the distal portion of a bone fracture. Accordingly, the threads 111 may include, but are not limited to, self-drilling threads.

In a self-drilling configuration, the distal end 110 may be configured as a point (e.g., prism shaped). As such, in this configuration, the use of a pilot hole may be eliminated.

The proximal portion 103 includes threads 109 and a proximal end 113. The threads 109 extends from the proximal end 113 to the transition portion 104. The threads 109 are structured to mate with/be complementary with internal threads of the compression device 105. In this regard, based on the threads chosen for the compression device 105, the threads 109 may vary from application-to-application (e.g., the pitch, lead, angle, coarseness, fineness, etc.). In operation, the threads 109 facilitate the movement of the compression device 105 via rotation towards the transition portion 104. The threads 109 also facilitate the removal of the compression device 105 off of the proximal end 113.

The distal portion 102 corresponds with a diameter 108 while the proximal portion 103 corresponds with a diameter 114. In one embodiment, the diameter 108 is larger than the diameter 114. In this configuration, the distal portion 102 acts like a "lag screw" and provides a compression force to reduce the fracture. However, in other embodiments, the body 101 has only one diameter (i.e., diameter 108 is equal to diameter 114) with the threads 111 being equal to the threads 109. In still further embodiments, any other combination is possible (e.g., a smaller diameter distal portion than proximal portion, larger and more coarse threads 109 than threads 111, etc.). Furthermore, as shown, the distal portion corresponds with a longitudinal length 122 and the proximal portion corresponds with a longitudinal length of 121. As shown, the longitudinal length 122 of the proximal portion 103 is approximately twice that of the longitudinal length 122 of the distal portion 102. In other embodiments, the length of the distal portion may be equal to or greater than the length of the proximal portion. As will be appreciated, many different configurations of the relative sizes (width/diameter) and lengths of the distal portion to the proximal portion of the implant are possible. All such variations are intended to fall within the spirit and scope of the present disclosure.

The transition portion 104 interconnects the distal portion 102 to the proximal portion 103. As shown, the transition portion 104 is a smooth or substantially smooth portion relative to the threads 111 and 109. However, in other embodiments, the transition portion 104 may be excluded from the body 101, may be of a varying diameter to accommodate differing diameter distal and proximal portions, etc.

As mentioned above, the spinal implant system 100 includes a compression device. As shown in FIGS. 1-3, the compression device is structured as a hexagonal locking nut 105. It should be understood that while shown as a hexagonal-shaped locking nut 105, the locking nut may have any shape (e.g., circular). As a locking nut, vibrations or movement in vivo are prevented from or substantially prevented from the loosening of the nut. This is intended to maintain the integrity of the spinal implant system 100. According to other embodiments, other types of nuts or compression devices may be used. For example, in one embodiment, a conventional nut may be used with a sealant (e.g., a bonding agent, etc.) that permanently or substantially permanently bonds the nut at a desired position along the proximal portion 103 upon the sealant curing. In this regard, if the nut is permanently or substantially permanently bonded at a desired location, rotation of the nut may advantageously work to undo the distal portion 102 from the distal bone fracture to remove the implant 101 entirely from the bone fracture.

The locking nut 105 includes a complementary set of internal threads that engage with the threads 109 of the proximal portion 103. Due to this threaded relationship, the locking nut 105 may be selectively placed longitudinally along the proximal portion 103 (e.g., closer to or further form the distal portion 102). Because the locking nut 105 includes an elastic, nylon, or other type of insert that substantially prevents the nut 105 from loosening after insertion (i.e., the locking feature of the locking nut), the nut may be selectively positioned along the proximal portion 103 at various desired times (e.g., at the time of insertion of the implant, at some point during the treatment process, and at the end of the treatment process to remove the implant). In turn, the compression force provided (i.e., to squeeze or compress the proximal bone fracture portion closer to the distal fracture portion) may be varied.

As shown, the locking nut 105 includes a rim 106 that defines a cavity 107. The rim 106 extends about a periphery of the cavity 107 to surround the cavity 107. The cavity 107 extends from the rim 106 towards a compression surface 115 of the nut 105. The depth that the cavity 107 extends towards the surface 115 is highly configurable based on the application. The cavity 107 allows a cutting device to enter the cavity 107 and cut, remove, or disconnect a desired piece of the proximal portion 103 in vivo. Because the cutting device is received within the cavity 107, the cutting device may sever or remove an unwanted portion of the proximal portion 103 at any point at or below the rim 106 (where below indicates a direction towards the compression surface 115). This protects the soft tissue and bone surrounding the implant 101 from any possible sharp ends that may remain after the unwanted part of the proximal portion is removed.

Figure 4:
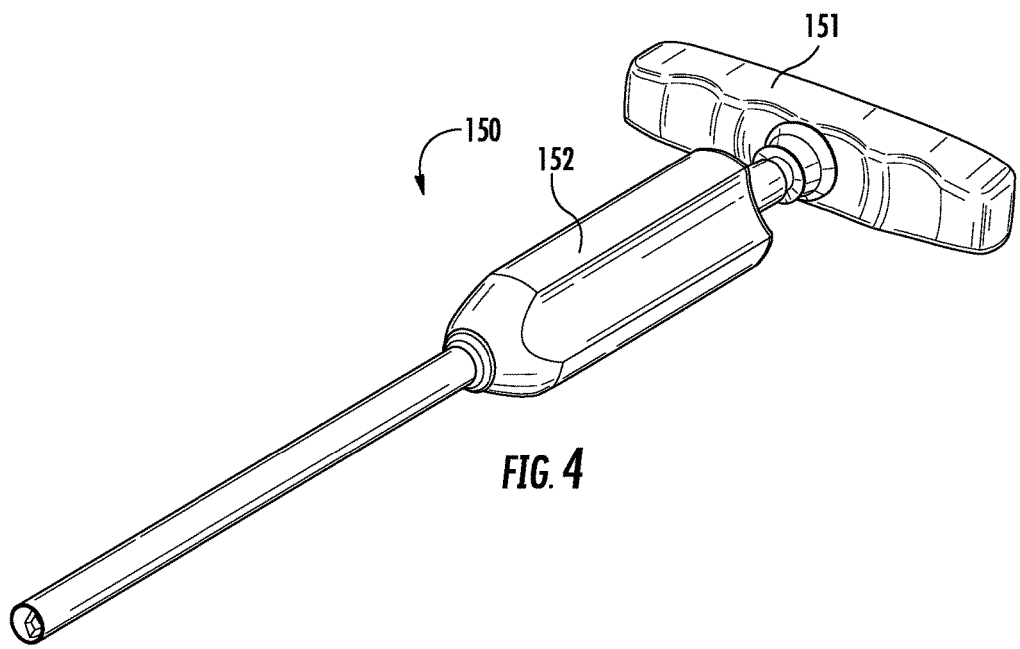
FIG. 4 is a perspective view of a cutting device for a spinal implant system, according to an exemplary embodiment.
Figure 5:
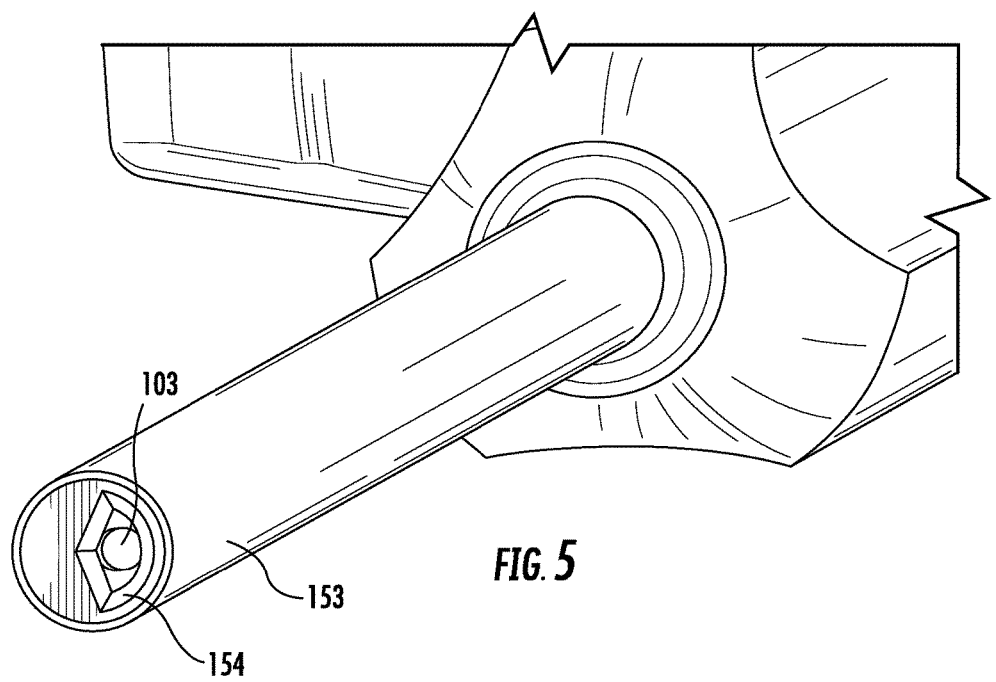
FIG. 5 is an end view the cutting device of FIG. 4.

Referring now to FIGS. 4-5, an example cutting device 150 for cutting a desired portion from the proximal portion 103 is shown according to one embodiment. As shown, the cutting device 150 includes a handle 151 and a grip 152. The handle 151 is coupled to a tube, while the grip 152 is coupled to another tube (e.g., cylinders, pipes, etc.). The tubes slide over the proximal portion 103 of the body 101 (see FIG. 5). Via rotation of the handle 151 and/or the grip 152, the hole defined by the tubes occludes (e.g., closes up). As a result, an unwanted portion of the proximal portion 103 is severed or removed from the body 101 (see FIG. 5).

Figure 6:
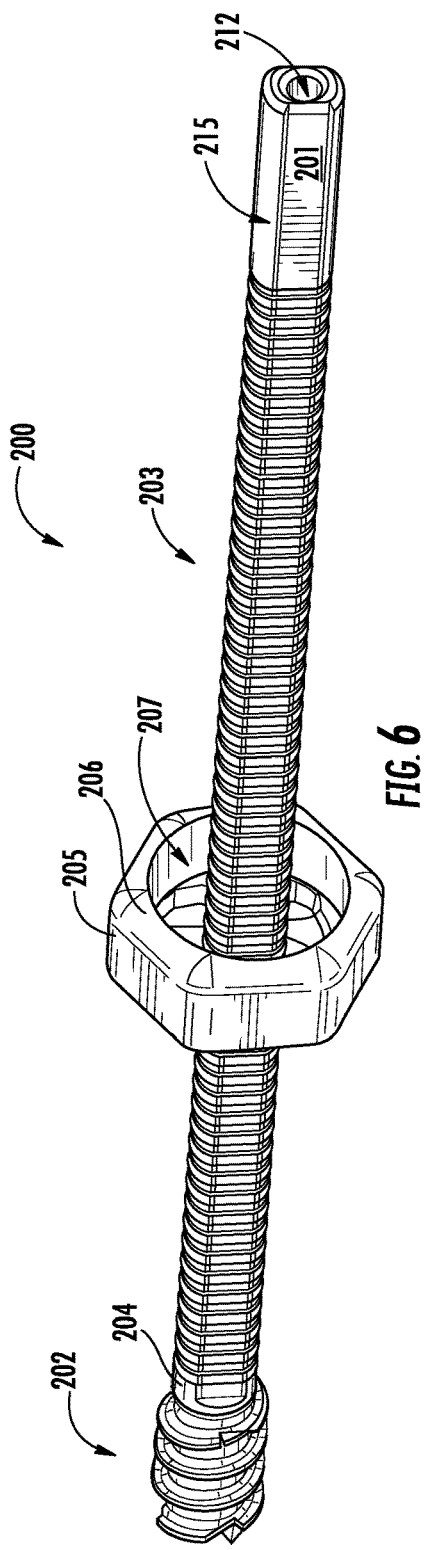
FIG. 6 is a perspective view of another spinal implant system, according to an exemplary embodiment.
Figure 7:
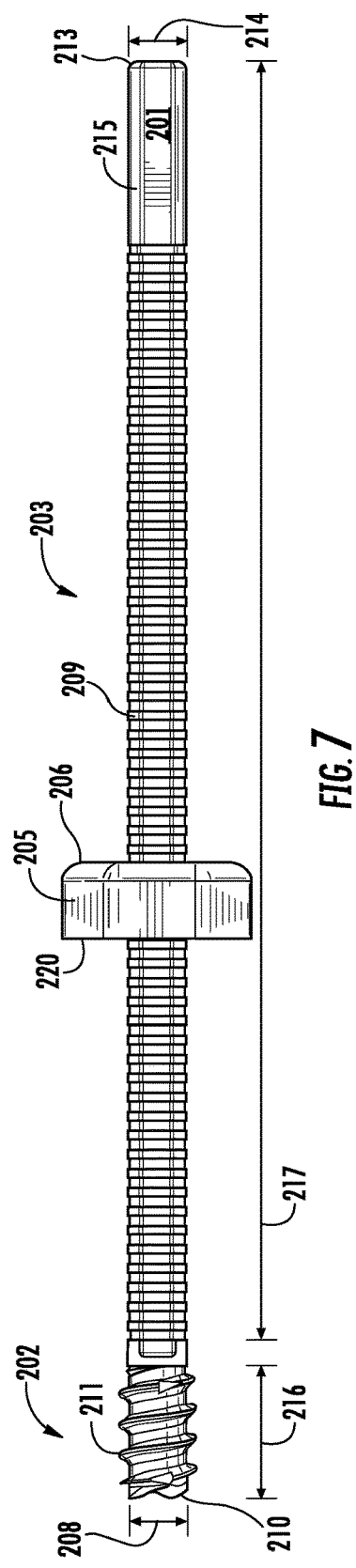
FIG. 7 is a side view of the spinal implant system of FIG. 6.

Referring now collectively to FIGS. 6-7, another spinal implant system 200 is shown according to an example embodiment. The spinal implant system 200 is substantially similar to the spinal implant system 100 of FIGS. 1-3. Like the spinal implant system 100, the spinal implant system 200 is used to reduce or immobilize bone fractures, particularly type II odontoid fractures. Accordingly, the spinal implant system 200 may be constructed from any type of biocompatible material like the spinal implant system 100, such as titanium or PEEK.

Like the implant system 100, the spinal implant system 200 includes an implant, shown as an elongated body 201, coupled to a compression device 205. The body 201 has a distal portion 202 and a proximal portion 203 interconnected by a transition portion 204. In one embodiment, the body 201 defines a passage 212 extending longitudinal within the body 201 from a distal end 210 to a proximal end 213. The passage 112 is structured to receive a guide member (e.g., a kirschner wire, a guide wire, a guiding pin, etc.) to insert the implant 100 on a desired trajectory to reduce or immobilize the bone fracture. In other embodiments, the implant 201 may exclude a passage (i.e., be a solid device).

The distal portion 202 includes threads 211 and the distal end 210. The distal end 210 is located furthest from the transition portion 204 and corresponds with one end of the body 201. As shown, the distal end 210 is a relatively flat or blunt surface. The distal portion 202 is structured to be at least partly received in the distal portion of the bone fracture. Due to the relatively flat or blunt distal end 210, after insertion in the bone fracture, the blunt distal end 210 is relatively less likely to adversely interact with the distal bone fracture to cause bone chips and the like. In this configuration, the threads 211 may be structured as lag-type threads (e.g., relative larger and coarser threads compared to conventional screw threads). In this regard, a pilot hole may be drilled in the distal and proximal bone fractures prior to inserting the distal portion 202. However, in other embodiments, the threads 211 may be structured as any thread type capable of joining or engaging with the distal portion of a bone fracture. Accordingly, the threads 211 may include, but are not limited to, self-drilling threads. In a self-drilling configuration, the distal end 210 may be configured as a point (e.g., prism shaped). In this configuration, the use of a pilot hole may be eliminated.

The transition portion 204 interconnects the distal portion 202 to the proximal portion 203. As shown, the transition portion 204 is a smooth or substantially smooth portion relative to the threads 211 and ribs 209 (described below). However, in other embodiments, the transition portion 104 may be excluded from the body 201, may be of a varying diameter to accommodate differing diameter or widths of the distal and proximal portions, etc. In still further embodiments, the transition portion 204 may include a surface texturing. All such variations are intended to fall within the spirit and scope of the present disclosure.

The distal portion 202 has a diameter 208 while the proximal portion 203 has a dimension 214. The dimension 214 corresponds to at least one of a cross-sectional longitudinal length or traverse width across the oval shape of the proximal portion 203. In one embodiment, the diameter 208 is larger than the dimension 214. In this configuration, the distal portion 202 acts like a "lag screw" and provides a compression force to reduce the fracture. In other embodiments, the proximal portion 203 is circular-shaped, where the dimension 214 corresponds with a diameter. In this configuration, the diameter of the proximal portion 203 may be one of the same or different from the diameter 208. However, in other embodiments, the body 201 has only one diameter (i.e., diameter 208 is equal to a diameter of the proximal portion). In still further embodiments, any other combination is possible (e.g., a smaller diameter distal portion than either a width or diameter of the proximal portion, etc.). Furthermore, as shown, the longitudinal length 217 of the proximal portion 203 is approximately five times the longitudinal length 216 of the distal portion 202. But, similar to the implant system 100, the relative longitudinal lengths of the proximal portion 203 to the distal portion 202 may vary based on the application (e.g., be greater than or less than a 5:1 longitudinal length relation of the proximal portion to the distal portion). All such variations are intended to fall within the spirit and scope of the present disclosure.

In contrast to the spinal implant system 100, the proximal portion 203 of the body 201 includes a flat portion 215 proximate the proximal end 213 and a plurality of ribs 209 (e.g., grooves, projections, etc.). The flat portion 215 represents a part of the proximal portion 203 where ribs 209 are excluded from. The flat portion 215 may facilitate the reception of the compression device onto the body 201. In some embodiments, the ribs 209 may extend to the proximal end 213, such that no flat portion 215 is included with the body 201.

Figure 8:
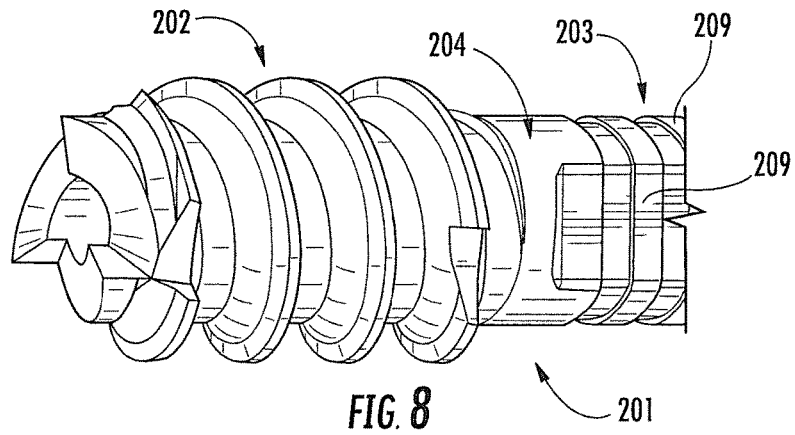
FIG. 8 is a close-up perspective view of the spinal implant system of FIG. 6.

As mentioned above, the proximal portion 203 includes a plurality of ribs 209 (e.g., grooves, projections, teeth, serrations, etc.). Referring now to FIG. 8, a close-up side view of the body 201 of FIGS. 6-7 is depicted, according to one embodiment. As shown in FIGS. 6-8, each of the ribs 209 completely surrounds a periphery of the proximal portion 203. In other embodiments, each or some of the ribs 209 may only partially surround the proximal portion 203. Further, the spacing between each adjacent rib may vary based on the application. In this regard, relatively closer-spaced ribs may provide additional control over the compression force provided by the compression device 205. In operation, rather than rotating the locking nut 105 to advance its position towards the distal portion 102 as in system 100, the compression device (shown as push nut 205) is incrementally pushed forward. Non-planar (i.e., curved) tongues or projections of the push nut 205 (described in more detail in regard to FIGS. 9-11) lock or secure the push nut 205 from moving retreating towards the proximal end 213 by engaging with a rib 209.

Figure 9:
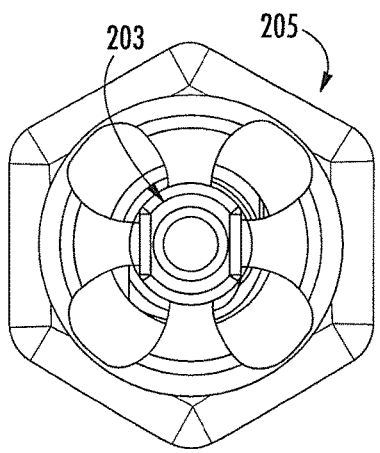
FIG. 9 is a top view of a compression device coupled to an implant for a spinal implant system, according to an exemplary embodiment.
Figure 10:
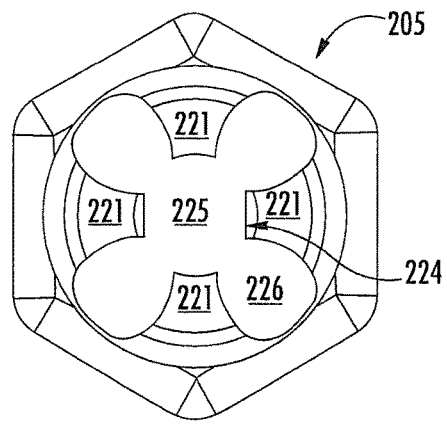
FIG. 10 is a top view of a compression device for a spinal implant system, according to an exemplary embodiment.
Figure 11:
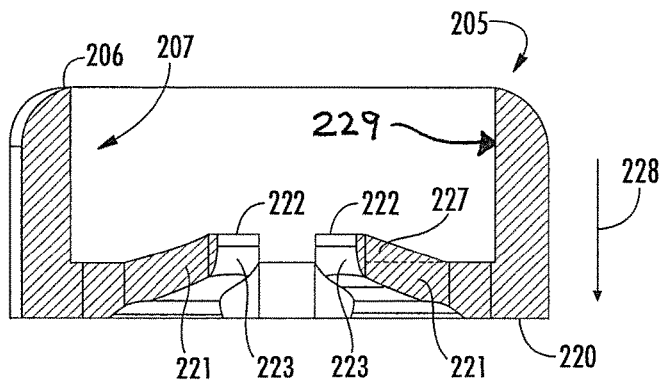
FIG. 11 is a cross-sectional view of a compression device for a spinal implant system, according to an exemplary embodiment.

Referring now to FIGS. 9-11, a push nut 205 for the spinal implant system 200 is shown according to one embodiment. As shown, the push nut 205 includes a top surface or rim 206 and an inner surface 229 that define a cavity 207. The cavity 207 extends from the rim 206 towards a compression surface 220. The compression surface 220 is structured to engage with a proximal bone part of the fracture to apply a compression force to that bone part. Accordingly, the compression surface 220 (like surface 115) may include surface texturing to provide for a better engagement with the proximal bone fracture. In other embodiments, the surface 220 may be substantially flat or be designed to include a coating to enhance the engagement.

The cavity 207 provides an access point for a cutting device, such as cutting device 150, to remove an unwanted portion of the proximal portion 203. In this regard, like the spinal implant system 100, the proximal portion 203 may be cut to a length that is at or below (in a direction towards the compression surface 220) the rim 206. Accordingly, this may reduce the likelihood that the proximal portion—due to not extending past the rim 206 of the nut 205—from adversely interfering and interacting with surrounding vascular structures. Due to the length-adjusting feature of the spinal implant system 200, the body 201 provides for modularity in bone fracture repair procedures because a surgeon or technician may cut the body 201 to the correct length for the fracture. This reduces the need of correctly selecting and predicting the right length implant for the fracture.

As shown, the push nut 205 includes a plurality of projections 221 (e.g., tongues, arms, flanges, etc.). The projections 221 extend towards a center of the push nut 205 to define an aperture 225 (e.g., hole, passage, etc.). In operation, the aperture 225 receives the proximal portion 203 of the body 201 (see FIG. 9). Accordingly, the size of the aperture 225 is structured to surround the proximal portion 203 of the body 201. The shape of the aperture 225 may be any shape desired as long as the projections 221 may engage with the ribs 209 and that the nut 205 may translate along the proximal portion 203. While the push nut 205 is shown to include four projections 221 that define cutouts 226 between adjacent projections 221, it should be understood that number of the projections 221 may vary (e.g., greater than or less than four) based on the application.

Furthermore, in some embodiments, no cutouts 226 may be included with the nut 205, such that only one unitary projection extends towards and surrounds the center of the nut to define the aperture 225.

As shown in FIG. 11, each of the projections 221 is at an angle 227 towards the rim 206. Further, each projection includes a top surface 222 and a transition surface 223. The top surface 222 is structured to engage with a rib 209 of the body 201. In operation, the push nut 205 is pushed, moved, or translated towards the distal portion 202 in a compression direction 228 (i.e., movement in the compression direction 228 acts to increase the compression force provided by the nut 205). The transition surface 223 is shown to include a curved shape, such that each rib 209 is relatively easily traversed in the compression direction 228. In some embodiments, each projection 221 may include a flexible characteristic, such that the projection flexes upwards towards the rim 206 as the nut 205 traverses a rib 209. However, due to the angle 227 and the relative flat characteristic of the surface 222, the surface 222 engages with a rib 209 after traversal to prevent or substantially prevent the nut 205 from moving back towards the proximal end 213. In this regard, each rib traversal is irreversible: the nut 205 cannot be pulled back towards the proximal end 213 to decrease the compression force. In certain embodiments, each tip 224 of each projection 221 may engage with the indent (i.e., the space between adjacent ribs) defined by the rib 209 that was traversed by the nut 205. The tips 224 may substantially prevent rotation of the nut 205 about the proximal portion 203. In this regard, rotation of the nut 205 also rotates the body 201. Accordingly, a technician or surgeon may utilize the nut 205 to facilitate removal of the implant assembly 200. Further, because the nut 205 is at least partly on the outer side (away from the bone fracture gap) of the proximal portion of the bone fracture (i.e., not within the proximal bone portion like the proximal portion 203 itself), the nut 205 is relatively more easily identified and, consequently, more easily engaged by a tool or a technician to facilitate the removal or adjust the location of the implant assembly.

As mentioned above, in other embodiments, the ribs 209 may not completely surround the periphery of the proximal portion 203. In this regard, the nut 205 may be rotated to engage with a rib at a desired position. However, the nut 205 may also be rotated to disengage the projections 221 from the rib when the nut is desired to be removed or to reduce the compression force provided by the nut 205. In this regard, the tips 224 may permit rotation of the nut 205 about the proximal portion 203.

Figure 12:
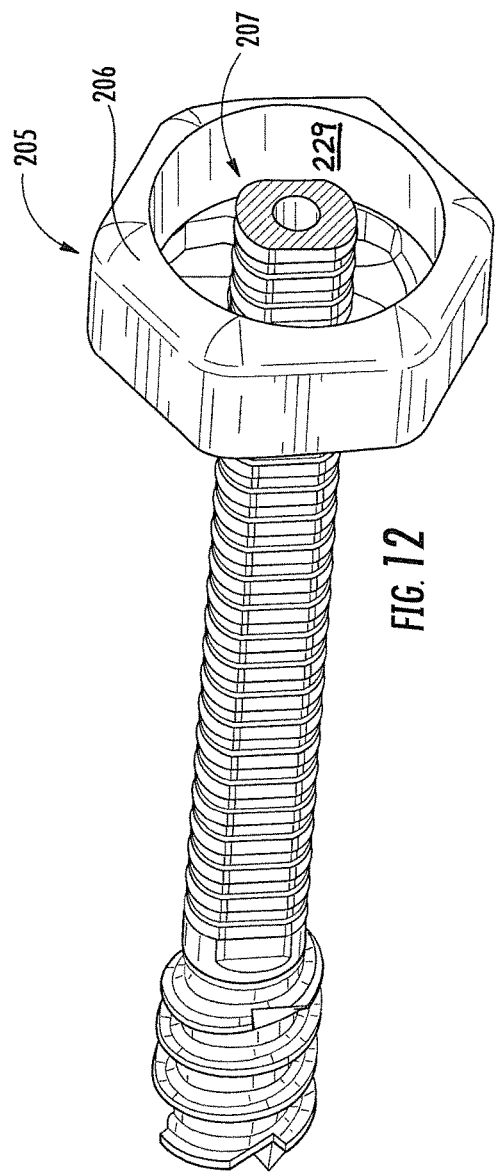
FIG. 12 is a perspective view of a spinal implant system with a proximal portion of the implant removed, according to an exemplary embodiment.
Figure 13:
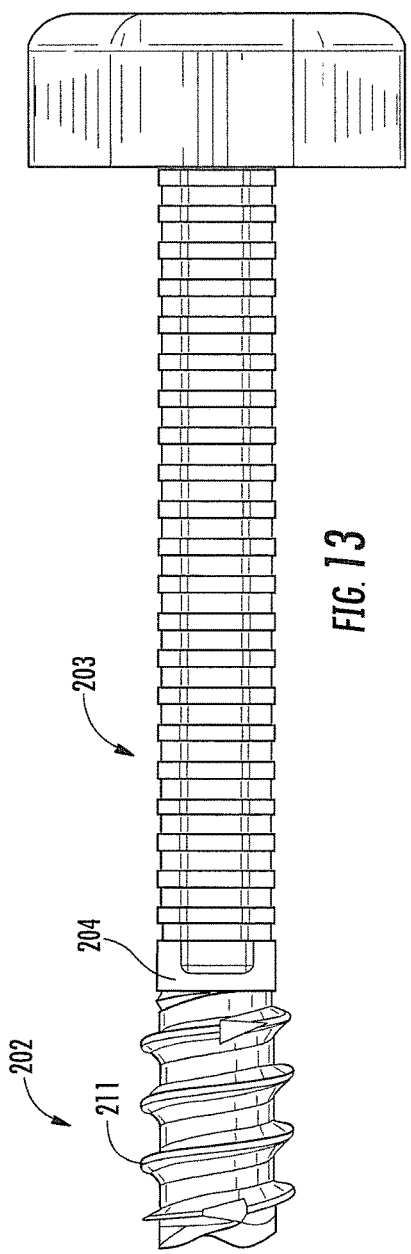
FIG. 13 is a side view of the spinal implant system of FIG. 12.

Referring now to FIGS. 12-13, a spinal implant system 200 is shown post-insertion and removal of the unwanted proximal portion. As shown, the remaining proximal portion 203 is at or below rim 206 of the push nut 205, and the remaining proximal portion 203 is spaced apart from the inner surface 229 (including the ribs 209). As mentioned above, by adjusting the proximal portion 203 to a length at or below the rim 206, any edges that may remain post-removal of the unwanted portion are substantially reduced from adversely impacting the bone and other vascular structures surrounding the bone fracture site.

Referring to FIGS. 14-19, a process of inserting the spinal implant system into a bone fracture is shown schematically, according to one embodiment. In the images depicted in FIGS. 14-19, the spinal implant system 200 as shown and described herein above (see, e.g., FIG. 6) is used to stabilize and reduce a type II odontoid bone fracture. FIGS. 14-19 represent before, during, and after insertion images of the spinal implant system 200 into the bone fracture. Prior to and after these processes, a plurality of other processes may occur. For example, first, a bone fracture site may be identified. Further, second, a pilot hole may be drilled across the fracture site through the distal fractured piece of bone's outer cortex. This operation may be done with or without a guide member (e.g., a guide wire). These processes and any other processes that may be used before, during, and after insertion of the spinal implant system 200 to accompany and/or complement the insertion process are intended to fall within the spirit and scope of the present disclosure.

Figures 14, 15:
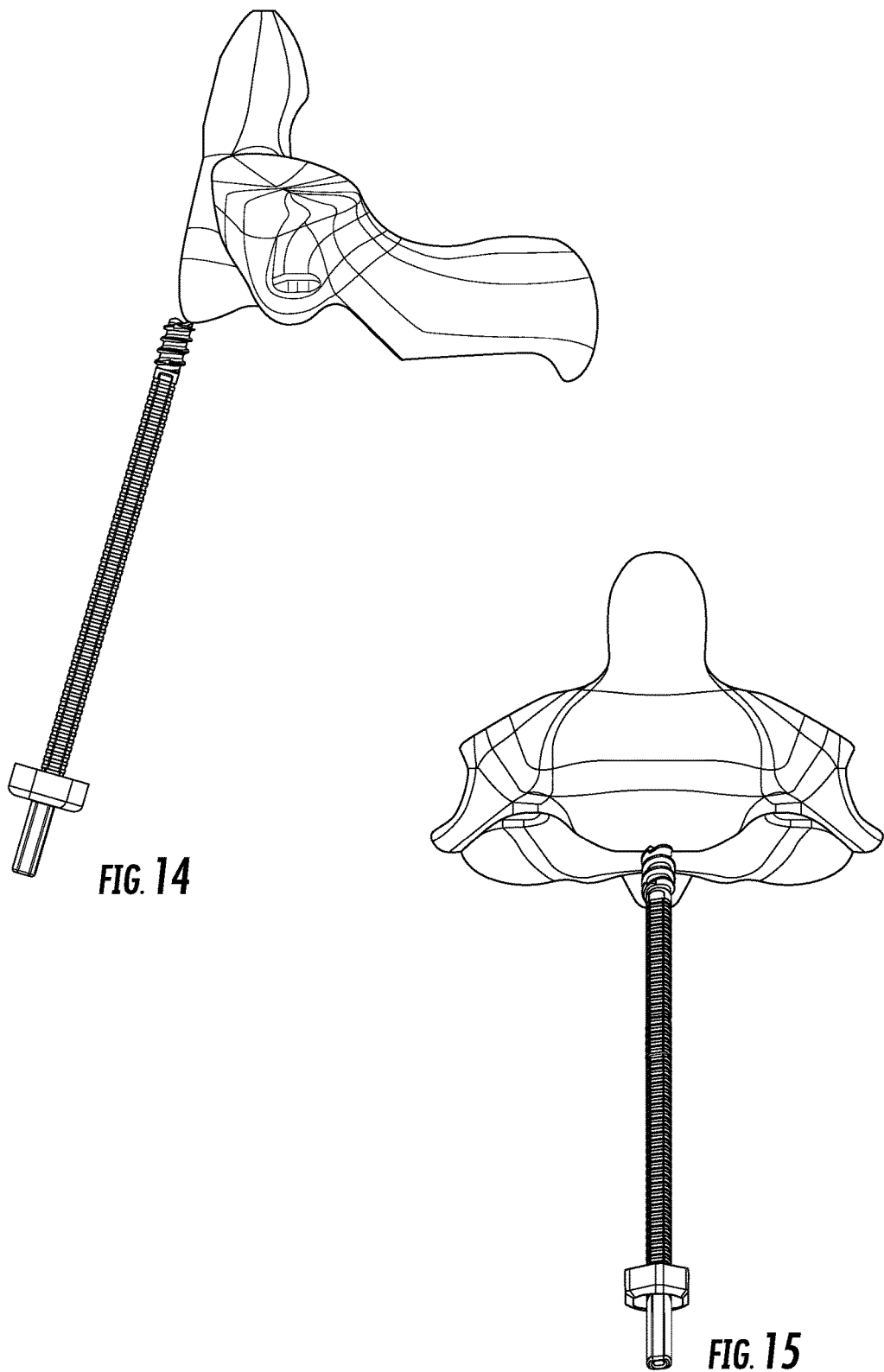
FIG. 14 is a side view of the spinal implant system of FIG. 6 pre-insertion along the C2 axis for reducing and stabilizing a type II odontoid fracture, according to an exemplary embodiment.
FIG. 15 is a top view of FIG. 14.
Figure 16:
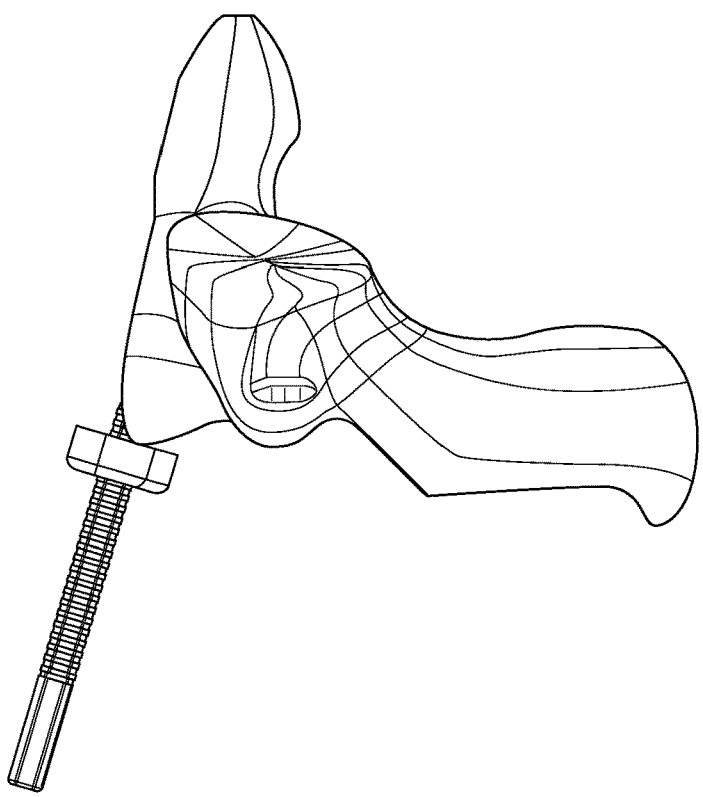
FIG. 16 is a side view of the spinal implant system of FIG. 6 during insertion along the C2 axis for reducing and stabilizing a type II odontoid fracture, according to an exemplary embodiment.
Figure 17:
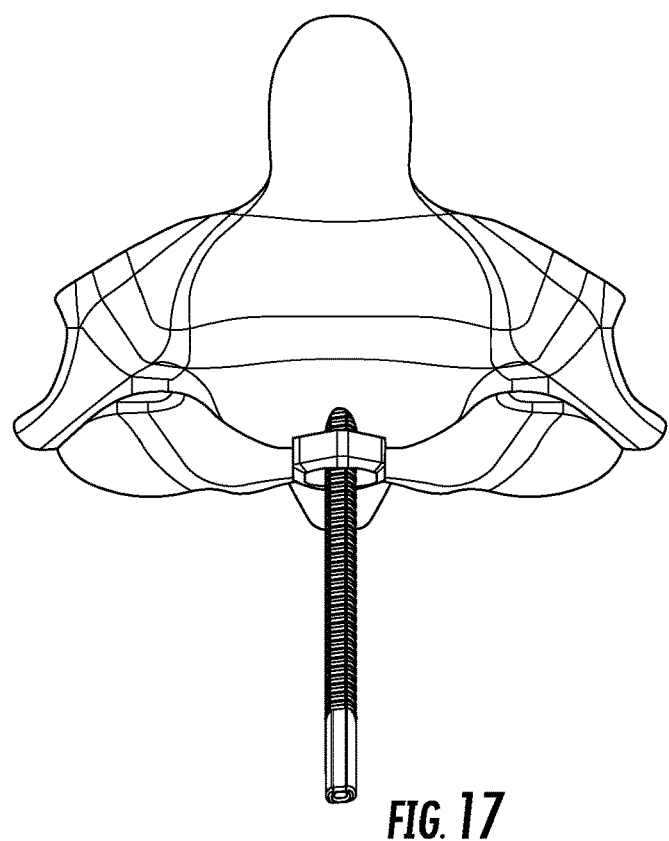
FIG. 17 is a top view of FIG. 16.
Figure 18:
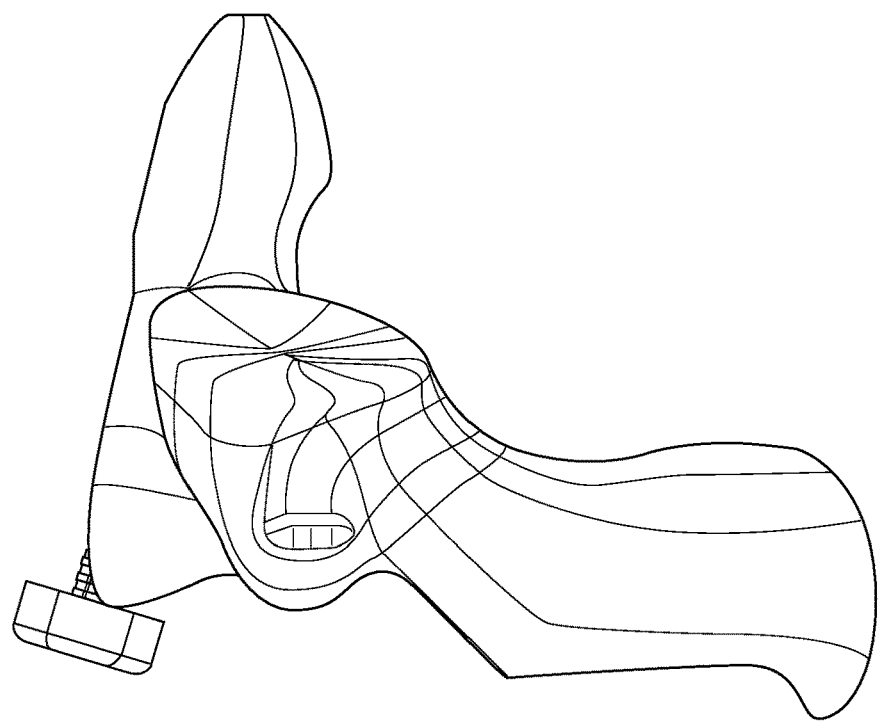
FIG. 18 is a side view of the spinal implant system of FIG. 6 after insertion along the C2 axis for reducing and stabilizing a type II odontoid fracture, according to an exemplary embodiment.
Figure 19:
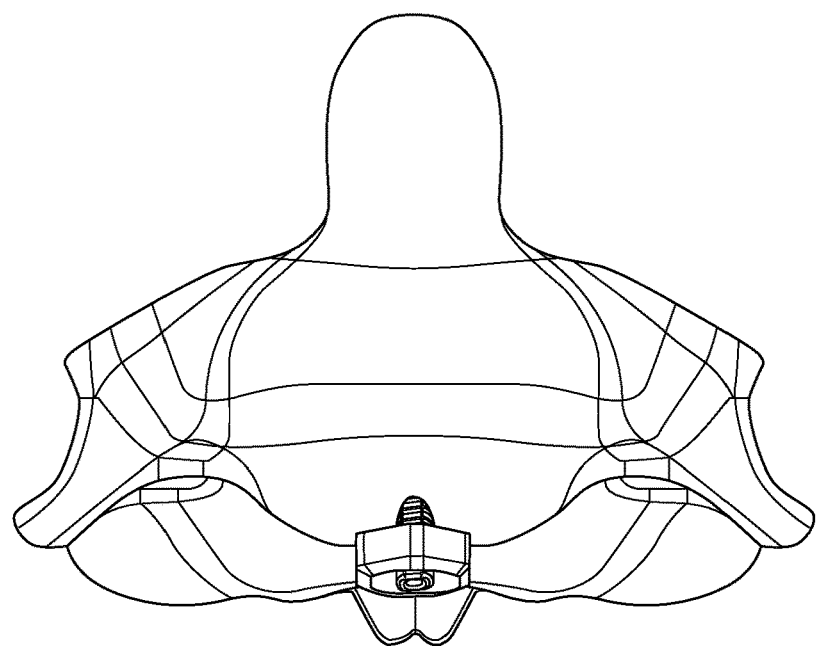
FIG. 19 is a top view of FIG. 18.

Referring now to FIGS. 14-15, a side view (FIG. 14) and top view (FIG. 15) of the spinal implant system 200 prior to insertion along the C2 axis to reduce and stabilize a type II odontoid fracture is shown according to one embodiment. FIG. 16 (side view) through FIG. 17 (top view) depict images of the distal portion of the implant being inserted into the proximal bone fracture part in a trajectory towards the distal bone fracture part. During insertion, the distal portion of the implant is inserted (e.g., screwed) into a position until the distal portion breaches the outer cortex of the distal most portion of the fracture. The compression device (e.g., push nut 205) is advanced down the proximal portion of the implant until the compression device makes contact with the most proximal portion of the fractured bone. The compression device is then tightened to help reduce the fracture and compress the proximal bone fragment with the distal bone fragment. Finally, the length of the proximal portion is adjusted to an appropriate length (e.g., via cutting device 150). The post-length adjustment of the proximal portion is shown in FIG. 18 (side view) through FIG. 19 (top view). As shown and described herein above, the cutting device may be used to cut the proximal portion to a length that is positioned within the cavity of the compression device to avoid adverse interference of the proximal portion with the surrounding vascular structures.

Figure 20:
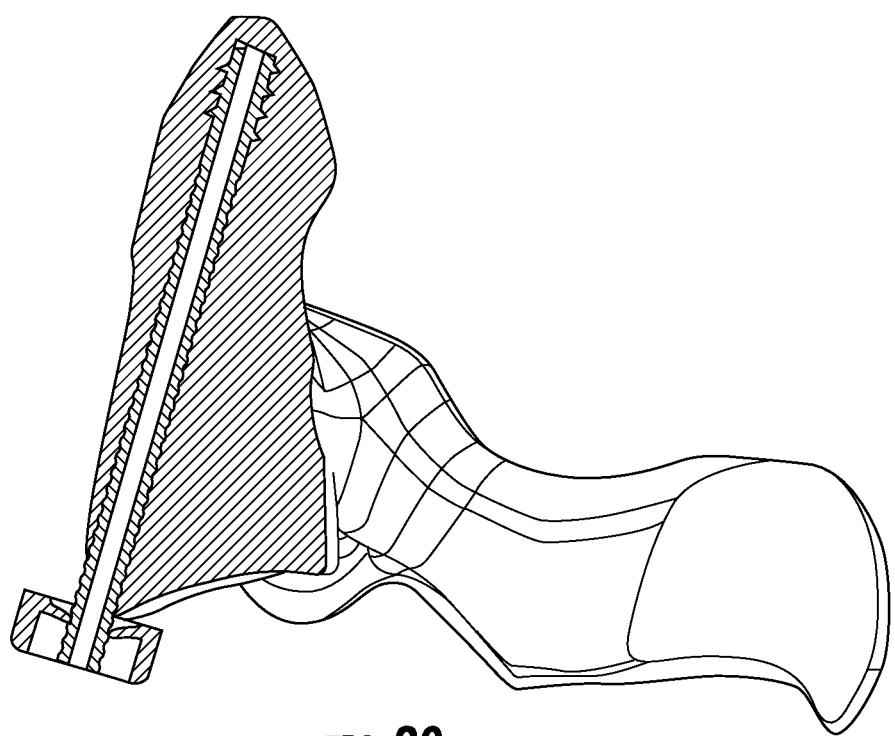
FIG. 20 is a cross-sectional view of FIG. 18, according to an exemplary embodiment.

FIG. 20 depicts a cross-sectional side view of FIG. 18. As shown, the proximal portion has been cut to be approximately flush with the rim 206 of the push nut 205. As also shown, the push nut 205 is in substantial contact with the proximal part of the bone fracture to apply a compression force in order to reduce and stabilize the bone fracture.

It should be noted that while a push nut and a locking nut are shown as compression devices for the spinal implant systems disclosed herein, that the present disclosure contemplates various other types of structures for the compression device. These structures may include, but are not limited to, a ratcheting system and the like. Further, while the cutting device is shown to actually cut a desired portion from the proximal portion of the implant, it should be understood that any other type of removal process or apparatus may be used to sever the unwanted portion from the proximal portion. All such processes and apparatus are intended to fall within the spirit and scope of the present disclosure. Furthermore, according to the present disclosure, the spinal implant system is used for immobilizing vertebrae of the spine including the cervical vertebrae of the spine and, more particularly, a C1 (atlas) vertebra of the spine relative to a C2 (axis) vertebra of the spine. While the spinal implant system is primarily shown and described herein with respect to the C1 and C2 vertebrae of the spine, it should be appreciated that the spinal implant may be used with other vertebrae of the spine, such that the spinal implant system may also be used in connection with other vertebral implants if desired.

It is also important to note that the construction and arrangement of the elements of the spinal implant system shown schematically in the embodiments is illustrative only.

Although only a few embodiments have been described in detail in this disclosure, those skilled in the art who review this disclosure will readily appreciate that many modifications are possible without materially departing from the novel teachings and advantages of the subject matter recited. For example, the shape and type of compression device may be varied as necessary to accommodate changes in the dimensions, shape and geometry of the other components of the spinal implant system. Accordingly, all such modifications are intended to be included within the scope of the present disclosure. Other substitutions, modifications, changes and omissions may be made in the design, operating conditions and arrangement of the preferred and other exemplary embodiments without departing from the spirit of the present disclosure.

Furthermore, the order or sequence of any process or method steps may be varied or re-sequenced according to alternative embodiments. Accordingly, the sequence and order of any methods or processes described herein is intended to be illustrative only, and not meant to be limiting.

What is claimed is:

1. A spinal implant system comprising:
   an elongated implant defining a distal portion and a proximal portion, the distal portion including a set of threads, the proximal portion comprising:
   a first curved outer surface;
   a second curved outer surface opposite the first curved outer surface;
   a first planar outer surface extending between the first curved outer surface and the second curved outer surface;
   a second planar outer surface opposite the first planar outer surface and extending between the first curved outer surface and the second curved outer surface;
   a plurality of ribs defining a plurality of indents, the ribs and indents extending continuously about the periphery of the proximal portion; and
   a compression device coupled to the proximal portion of the elongated implant, the compression device movable from an end of the proximal portion towards the distal portion of the elongated implant, wherein the compression device is structured to apply a compression force to a proximal part of the bone fracture, wherein the compression device comprises:
   an inner surface;
   an upper surface;
   a compression surface adapted to engage bone;
   a cavity extending from the upper surface toward the compression surface and at least partially defined by the inner surface;
   a plurality of projections defining a passage therebetween, each projection extending from the compression surface and the inner surface toward the upper surface and having a top surface located within the cavity and spaced apart from the upper surface;
   wherein the proximal portion of the elongated implant extends through the passage and into the cavity on the compression device so that the top surfaces on the plurality of projections engage with a rib of the plurality of ribs, and wherein the inner surface of the compression device is spaced apart from the plurality of ribs of the proximal portion.

2. The spinal implant system of claim 1, wherein after the compression device is positioned at a desired location along the proximal portion, a portion of the proximal portion of the elongated implant is removed so that an end of the remaining proximal portion is disposed within the cavity between the upper surface and the compression surface and does not extend beyond the upper surface of the compression device.

3. The spinal implant system of claim 1, wherein the elongated implant defines a passage extending longitudinally and coaxially within the elongated implant from a first end of the implant to a second end of the implant, wherein the passage is configured to receive a guide member.

4. The spinal implant system of claim 1,
   wherein adjacent ribs of the plurality of ribs are separated by the indents, the indents are configured to receive the tips of top surfaces of the plurality of the projections;
   wherein the projection permits traversal of each rib in the plurality of ribs in a first direction towards the distal portion, and wherein the projection prevents translation of the compression device in a second direction towards the proximal portion after the projection has traversed at least one rib.

5. The spinal implant system of claim 4, wherein the distal portion includes a diameter, and the proximal portion includes a dimension that is smaller than the diameter of the distal portion.

6. The spinal implant system of claim 1, wherein the compression device is structured to provide a relatively greater compression force to the bone fracture as the compression device is moved from the proximal portion towards the distal portion of the elongated implant.

7. An implant system for reducing or immobilizing bone fractures, the implant system comprising:
   an elongated implant including a distal portion and a proximal portion, the distal portion including a set of threads, and the proximal portion including a plurality of ribs, a pair of opposing curved outer sides separated by a pair of opposing planar outer sides the plurality of ribs extending at least across the planar outer sides; and
   a compression device coupled to the proximal portion of the elongated implant, the compression device movable from an end of the proximal portion towards the distal portion of the elongated implant, wherein the compression device is structured to apply a compression force to a proximal part of the bone fracture, wherein the compression device comprises:
   an inner surface;
   an upper surface;
   a compression surface that engages the bone fracture;
   a cavity defined by the inner surface, the upper surface, and the compression surface;
   a plurality of projections defining a passage therebetween, each projection having a top surface disposed within the cavity and spaced apart from the upper surface;
   wherein the proximal portion of the elongated implant extends through the passage and into the cavity on the compression device so that the top surfaces on the plurality of projections engage with a rib of the plurality of ribs, and wherein the inner surface of the compression device is spaced apart from the proximal portion.

8. The implant system of claim 7, wherein the ribs define a plurality of grooves located between adjacent ribs, wherein the ribs and grooves extend continuously around the periphery of the proximal portion.

9. The implant system of claim 7, wherein the plurality of projections permit translation of the compression device in a first direction towards the distal portion, and wherein the plurality of projections prevent translation of the compression device in a second direction towards the proximal portion after the plurality of projections have traversed at least one rib in the plurality of ribs.

10. The implant system of claim 7, wherein a cross-section of the proximal portion is oblong, and wherein each of the plurality of ribs extend continuously around the periphery of the proximal portion.

11. The implant system of claim 7, wherein the proximal portion includes an end opposite the distal portion; wherein the end of the proximal portion is located between the upper surface and the compression surface of the compression device after the compression device is positioned at a desired location along the proximal portion.

12. The implant system of claim 7, wherein the engagement of the projections and ribs prevents rotation of the compression device relative to the elongated implant such that rotation of the compression device causes rotation of the elongated implant.

13. The implant system of claim 7, wherein the plurality or ribs do not completely surround the periphery of the proximal portion so that the compression device may be rotated to disengage the projections from the rib.

14. The implant system of claim 7, wherein each of the plurality of projections includes an angled transition extending between the compression surface and the top surface.

15. The implant system of claim 14, wherein the plurality of projections comprises four projections, and wherein the compression device further comprises four cut-outs, whereby one cut-out is located between adjacent projections.

16. A method of reducing or immobilizing bone fractures, the method comprising:
providing an implant, the implant having an elongated body with a distal portion and a proximal portion, the proximal portion having a pair of opposed curved outer sides separated by a pair of opposed planar outer sides, and a plurality of alternating ribs and indents extending across the curved and planar outer sides about the periphery of the proximal portion;
providing a compression device, the compression device having an upper surface, an inner surface, a compression surface, a cavity defined by the inner surface, the upper surface, and the compression surface, and a plurality of projections defining a passage therebetween, each projection having a top surface disposed within the cavity and spaced apart from the upper surface;
inserting the distal portion of the elongated body into a distal part of a bone fracture;
inserting the proximal portion of the implant through the passage so that a first projection and second projection engage the ribs on the opposed curved outer sides and so that a third projection and fourth projection engage the ribs on the opposed planar outer sides, between the top surfaces of the projections, and into the cavity on the compression device;
moving the compression device along the proximal portion of the elongated body toward the distal portion to make contact with a proximal part of the bone fracture; and
adjusting a position of the compression device to control a compression force provided by the compression device on the proximal portion of the bone fracture;
removing an unwanted portion of the proximal portion from the elongated body, wherein an end of a remaining portion of the proximal portion is disposed within the cavity and spaced apart from the upper surface of the compression device and the inner surface of the compression device.

17. The method of claim 16, wherein moving the compression device closer to the distal portion comprises translating the compression device along an axis of the implant and increases the compression force provided by the compression device.

18. The method of claim 16, wherein the compression device includes one of a push nut and a locking nut.

19. The method of claim 16, wherein a diameter of the distal portion is greater than at least one of a cross-sectional width, a cross-sectional length, or a diameter of the proximal portion.

20. The implant system of claim 16, wherein the pair of opposed curved outer sides and the pair of opposed planar outer sides provide the proximal portion with an oblong cross-section.

* * * * *